(12) United States Patent  (10) Patent No.: US 8,638,995 B2
Greenstein et al.  (45) Date of Patent: Jan. 28, 2014

(54) OPTICAL SPECULUM

(75) Inventors: Lior Greenstein, Tel Aviv (IL); Gilad A. Davara, Rehovot (IL); Gad Ganon, Yad Hana (IL); David Aviv, Hadera (IL)

(73) Assignee: Illumigyn Ltd., Neve Ilan (IL)

( * ) Notice: Subject to any disclaimer, the term of this patent is extended or adjusted under 35 U.S.C. 154(b) by 604 days.

(21) Appl. No.: 12/943,170

(22) Filed: Nov. 10, 2010

(65) Prior Publication Data

US 2011/0112408 A1    May 12, 2011

Related U.S. Application Data

(60) Provisional application No. 61/259,663, filed on Nov. 10, 2009.

(51) Int. Cl.
*G06K 9/00* (2006.01)

(52) U.S. Cl.
USPC .......................................................... 382/128

(58) Field of Classification Search
USPC .......................................................... 382/128
See application file for complete search history.

(56) References Cited

U.S. PATENT DOCUMENTS

| | | | |
|---|---|---|---|
| 4,491,131 A | 1/1985 | Vassiliadis | |
| 4,905,670 A | 3/1990 | Adair | |
| 5,143,054 A | 9/1992 | Adair | |
| 5,179,938 A | 1/1993 | Lonky | |
| 5,251,613 A | 10/1993 | Adair | |
| D395,084 S | 6/1998 | Krauter et al. | |
| 5,791,346 A | 8/1998 | Craine et al. | |
| 5,836,872 A | 11/1998 | Kenet et al. | |
| 5,840,012 A | 11/1998 | Krauter et al. | |
| 5,846,249 A | 12/1998 | Thompson | |
| D416,088 S | 11/1999 | Krauter et al. | |
| 6,068,593 A | 5/2000 | Krauter et al. | |
| 6,101,408 A | 8/2000 | Craine et al. | |
| 6,106,457 A * | 8/2000 | Perkins et al. ................ 600/175 |
| 6,147,705 A | 11/2000 | Krauter et al. | |
| 6,277,067 B1 | 8/2001 | Blair | |
| 6,346,085 B1 | 2/2002 | Schiffman | |
| 6,359,644 B1 | 3/2002 | Salvati | |
| 6,496,718 B1 | 12/2002 | Lonky | |
| 6,595,917 B2 | 7/2003 | Nieto | |
| 6,712,761 B2 | 3/2004 | Borodulin et al. | |
| 6,766,184 B2 | 7/2004 | Utzinger et al. | |
| 2004/0064053 A1 | 4/2004 | Chang et al. | |
| 2004/0186355 A1 | 9/2004 | Strong et al. | |
| 2005/0234305 A1 * | 10/2005 | Licciardi ...................... 600/221 |
| 2006/0122463 A1 | 6/2006 | Klaassen | |
| 2006/0276693 A1 | 12/2006 | Pacey | |

(Continued)

FOREIGN PATENT DOCUMENTS

WO    WO 98/25512    6/1998

*Primary Examiner* — Tom Y Lu
(74) *Attorney, Agent, or Firm* — Brooks Kushman P.C.

(57) ABSTRACT

A system for direct imaging and diagnosing of abnormal cells in a target tissue includes a disposable optical speculum and an image acquisition system having the speculum assembled on and mechanically secured thereto. The image acquisition system is arranged to capture at least one of a single image or multiple images or video of cells within the target tissue using at least one of bright field or dark field ring illumination divided into independently operated segments to obtain a plurality of data sets. An image analysis and control unit in communication with the image acquisition system analyzes the data sets and applies algorithms to the data sets for diagnosing abnormal cells.

19 Claims, 5 Drawing Sheets

(56) References Cited

U.S. PATENT DOCUMENTS

| | | | |
|---|---|---|---|
| 2007/0112273 A1* | 5/2007 | Rogers | 600/475 |
| 2007/0161876 A1 | 7/2007 | Bambot et al. | |
| 2008/0045799 A1* | 2/2008 | Whitehead et al. | 600/178 |
| 2008/0208006 A1* | 8/2008 | Farr | 600/178 |
| 2008/0306345 A1 | 12/2008 | Balas | |
| 2008/0312508 A1 | 12/2008 | Shulman | |
| 2009/0082695 A1 | 3/2009 | Whitehead | |
| 2009/0177044 A1 | 7/2009 | Cohen et al. | |
| 2009/0205665 A1* | 8/2009 | Tanaka et al. | 128/205.27 |
| 2009/0216088 A1 | 8/2009 | Danna et al. | |
| 2009/0326331 A1 | 12/2009 | Rosen | |

* cited by examiner

OPTICAL SPECULUM

CROSS-REFERENCE TO RELATED APPLICATIONS

This application claims the benefit of U.S. provisional Application No. 61/259,663 filed Nov. 10, 2009, the disclosure of which is incorporated in its entirety by reference herein.

TECHNICAL FIELD

This invention relates to an optical speculum, such as for use in colposcopy, gynecology examination, and detecting and/or removing abnormal cells.

BACKGROUND

Uterine cervical cancer is the second most common cancer in women worldwide, with nearly 500,000 new cases and over 270,000 deaths annually. Colposcopy is a medical diagnostic method that is used to detect cervical intraepithelial neoplasia (CIN) and cancer, together with a cytological screen (Papanicolaou smear; i.e., Pap smear). Colposcopy is a medical diagnostic procedure for viewing the cervix and the tissues of the vagina and vulva, and is a common gynecology procedure following an abnormal Pap smear. A colposcope is a low powered binocular microscope with a light source, magnifying lens, and imaging sensor for viewing and inspection of internal cavities, and may include video.

Cervical cancer precursor lesions and invasive cancer exhibit certain distinctly abnormal morphologic features that can be identified by colposcopic examination. The purpose of this examination is to identify and rank the severity of lesions, so that biopsies representing the highest grade abnormality can be taken, if necessary. During the examination, a 3-5% acetic acid solution is applied to the cervix, causing abnormal and metaplastic epithelia to turn white. A green filter may be used to accentuate vasculature.

Today, the standard procedure for a gynecological exam invoices the use of a standard speculum with which the physician does a visual examination of the interior vaginal cavity, without any control of optimal illumination or proper optical magnification, thus creating the possibility of missing the detection of abnormal cells.

BRIEF DESCRIPTION OF THE DRAWINGS

In order to understand the invention and to see how it may be carried out in practice, embodiments will now be described, the way of non-limiting examples only, with reference to the accompanying drawings, in which.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The invention, hereinafter the "SpeculuView" system, is an apparatus comprising an optical disposable speculum, an image acquisition system comprising a treatment module and an image analysis and control unit.

The described system may be used as a colposcopy imaging system. It may comprise a treatment module to apply an ablation technique of abnormal cells (e.g., cancerous cells) in the examined area (e.g., cervical uterine).

One of the aims of the SpeculuView system is to assure detailed observation with high resolution of objects located within a relatively wide area of the examined area (e.g., uterine cervix cavity), and enable accurate ablation of abnormal cells (e.g., cancerous cells in the uterine cervix).

Low cost and high resolution colposcopy could have a direct impact on improving women's health care, reducing examination costs and avoidance of embarrassment. This low-cost hand-held image acquisition device can also assist the expert colposcopist, and improve screening cost-effectiveness in developing countries.

Colposcopy is the leading diagnostic method that is used to detect Cervical Intraepithelial Neoplasia (CIN) and cancer, together with cytological screen (Papanicolaou smear—Pap Smear).

The purpose of a colposcopic examination is to identify and rank the severity of lesions, so that biopsies representing the highest-grade abnormality can be taken, if necessary. A green filter may be used to accentuate vasculature. During the examination, a 3-5% acetic acid solution is applied to the cervix, causing abnormal and metaplastic epithelia to turn white. Cervical cancer precursor lesions and invasive cancer exhibit certain distinctly abnormal morphologic features that can be identified by colposcopy examination.

Figure 1A:
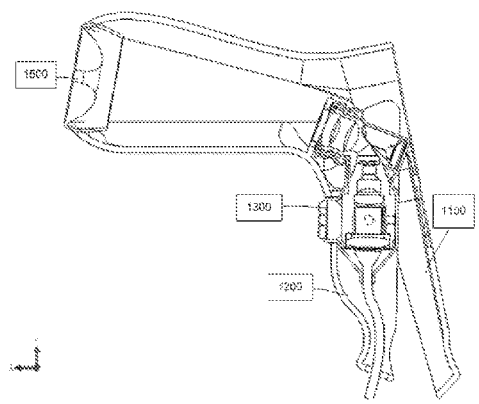
FIG. 1a is an assembly cross section view, including the inspection area, and including an example of a possible inspected area, the uterine cervix. 1100—Illustrates a cross section view of the upper part of the optical disposable speculum; 1200—Illustrates a cross section view of the lower part of the optical disposable speculum; 1300—Illustrates a cross section view of the image acquisition system; 1500—Illustrates a cross section view of a possible inspected area, the uterine cervix.
Figure 1B:
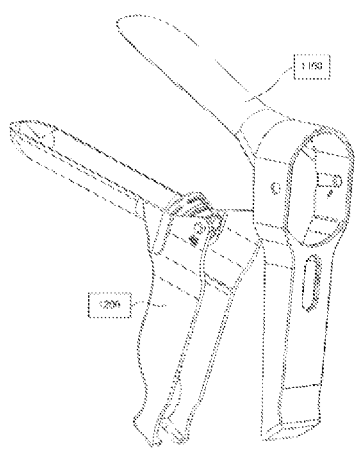
FIG. 1b is an exploded view of the optical disposable speculum including a lower part and an upper part. 1100—Illustrates the upper part of the optical disposable speculum; 1200—Illustrates the lower part of the optical disposable speculum.

In the SpeculuView system, the optical disposable speculum is assembled on the image acquisition system on each examination. It protects the patient from cross contamination. It creates a clean environment for the image acquisition system, to prevent it from being contaminated (FIG. 1*a* and FIG. 1*b*). This design enables a shortened time between examinations.

There are two optional image acquisition designs presented herein: A single imaging sensor system comprised of a color CMOS or CCD (FIG. 5*a*) and an illumination system based on LEDs or LD (Laser Diode), and a dual imaging sensors system design comprised of two different CMOS or CCD—Color and monochrome (FIG. 5*b*) and an illumination system based on LEDs or LD (Laser Diode).

Figure 3A:
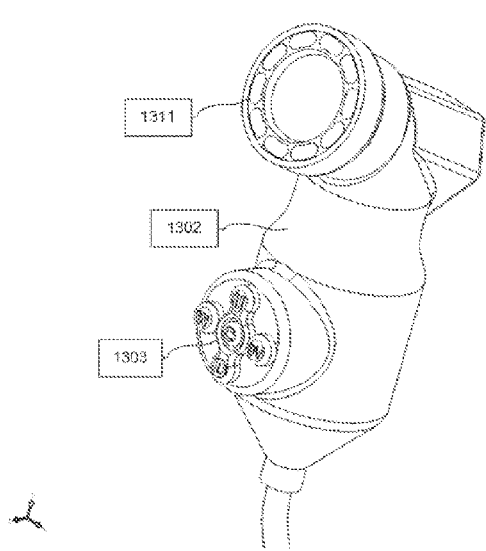
FIG. 3a illustrates the image acquisition system—Outside view. 1302—Image acquisition system body; 1303—Camera head operating buttons; 1311—Dark field illumination LEDs ring.
Figure 3B:
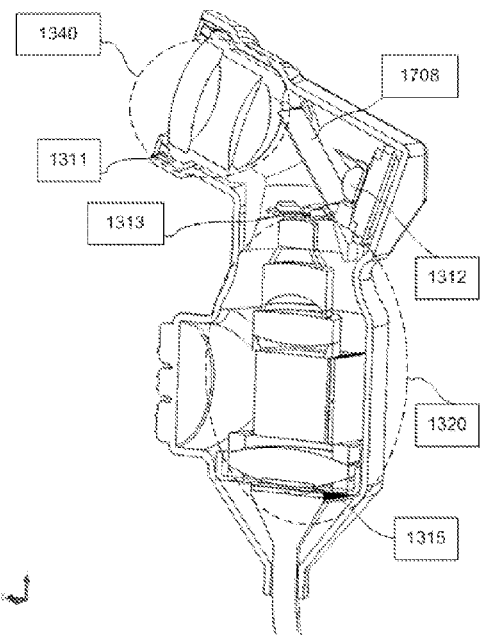
FIG. 3b illustrates the image acquisition system—Inside view. 1311—Dark field illumination LEDs ring; 1312—UV or IR LED illumination; 1313—Bright field illumination LEDs ring; 1315—Imaging sensor area; 1708—Dichroic mirror; 1340—Front group lens; 1320—Rear group lens.
Figure 4:
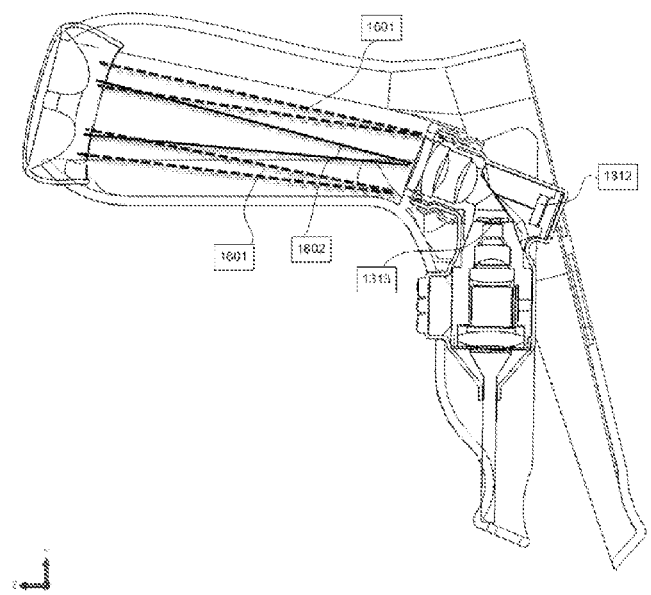
FIG. 4 illustrates the illumination rays by showing a cross section view of the SpeculuView system (optical disposable speculum assembled on the image acquisition system). 1601—Dark field illumination rays; 1602—Bright field illumination rays; 1312—Multi spectral (e.g., UV or IR LED) illumination; 1313—Bright field illumination LEDs ring.

The illumination system comprises bright field illumination 1313 (shown in FIG. 3*b*, FIG. 4), dark field external ring illumination 1311 (shown in FIG. 3*a*, FIG. 3*b*), a UV LED source for fluorescence and or autofluorescence and/or a multi spectral source 1312 (e.g., white and or IR LEDs) (shown in FIG. 3*b*, FIG. 4).

The illumination system comprises UV LED source light for fluorescence image analysis in addition to bright and dark field white light sources. Based on previous research, abnormal cancerous cells are highly emphasized by this kind of illumination. The optical design comprises a dichroic mirror that transmits the light below 400 nm and reflects the light above 440 nm. This beam splitter is well suited for such fluorescence measurements.

In order to reach depth perception, there are three main features in this system.

1) The system has the option for a large depth of field.

2) Using the contiguous zoom feature, the system can receive a sequence of different images of the same (X,Y) position at different focal planes. In this method, good perception of the inspected object depth can be attained.

3) The system applies dark field illumination in different angles using an external illumination ring element. As a non-limiting example, the system may be designed to divide and control the illumination ring (e.g., two sections). By use of one section of the ring in the first image and a second section of the ring in the second image the system may provide depth perception of the inspected object.

High resolution over the whole field is assured in order to insure detection of all cancerous cells in one image.

Using these three methods the system can identify, for example, the tumor cell thickness, and its surface topology.

Figure 7:
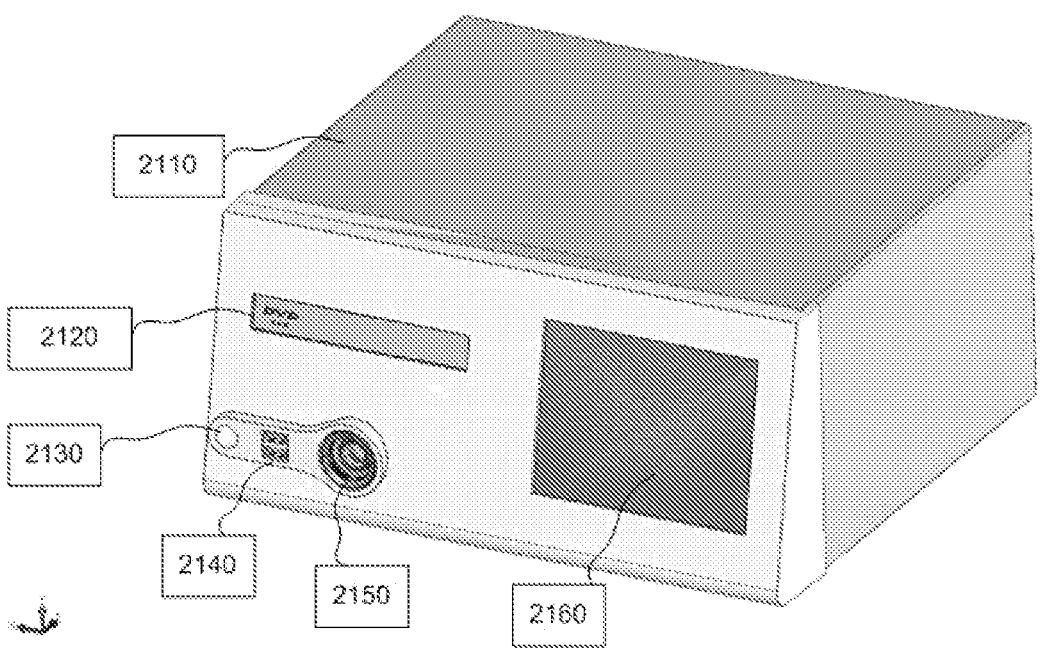
FIG. 7 illustrates the image analysis and control unit. 2110—Illustrates the box of control and analysis system; 2120—Illustrates the optical drive, read-write (e.g. DVD/+-RW, Blu-Ray/+-RW); 2130—Illustrates the On/Off operating button; 2140—Illustrates the peripheral connection to the camera head (e.g., USB); 2150—Illustrates the image acquisition cable connector; 2160—Illustrates the LCD screen (e.g., touch LCD) for system function operation.

The image acquisition system is connected to the image analysis and control unit (FIG. 7). The image analysis and control unit is a software package which may be implemented on special design hardware or a standard PC with custom hardware.

The image acquisition system may comprise an integrated laser ablation module for treatment of abnormal cells (e.g., cancerous cells in the uterine cervix).

The image acquisition system may acquire multi spectral images and/or live video.

The image analysis and control unit automatically adjusts the intensity of each illumination mode independently (i.e., white (bright field and or dark field illumination), multi spectral illumination (e.g. UV and or IR)).

Data acquired from the examined area (e.g., uterine cervix) by the image acquisition system is analyzed by the image analysis and control unit which provides tissue diagnosis. In case there are abnormal cells, the image analysis and control unit identifies the suspicious regions which should be treated (e.g., cell ablation system).

In order to prevent stray light, the optical disposable speculum window may be designed with a layer of elastic material which creates a fine-tuned coupling between the optical disposable speculum and the image acquisition system. This design compensates the mechanical, manufacturing and assembly tolerances 1221 (shown in FIG. 2b).

The optical disposable speculum may be coupled with an RFID (Radio Frequency Identification) unique tag. The image analysis and control unit will assure the use of a brand new optical disposable speculum for each patient per each examination. The RFID tag number is identified uniquely by a serial number/lot number. The tag number which is coupled with the optical disposable speculum will be specified in the patient examination file. It can also assure the use of a brand new optical disposable speculum for each patient per each examination by snaps 1212 which break after severance with the image acquisition system (shown in FIG. 3a).

The image analysis and control unit is able to analyze white and/or multi spectral images taken under the use of reflectance and auto-fluorescence reagents (i.e., contrast agents).

The image analysis and control unit is based on an open, modular, and feature-based architecture. Analysis methods are designed for use with one or more imaging sensors, white and/or multi spectral illumination types.

The image analysis and control unit may provide methods based on unique algorithms for accurate removal of abnormal cells (e.g., identifying their margin).

The algorithm in the image analysis and control unit will create a map of contours, namely edges between healthy and abnormal cells.

Reflectance and/or fluorescence images are acquired from the abnormal cells. Optionally, a short flash may acquire the reflectance and/or fluorescence images. Various reflectance and fluorescent images may be acquired under the same, or different, configurations of illumination.

Abnormal cells may be destroyed by ablation. The ablation procedure will be operated automatic or by manual control of the set of adjustable mirrors controller that uses output indications of candidate abnormal cells. Upon completion of destruction by ablation, additional reflectance or fluorescence images will be acquired to verify the completion of the procedure, resulting in no abnormal cells being left.

The laser ablation system may comprise an imaging sensor, flexible/solid optical fiber, laser system, set of mirrors near the laser head and near the beam splitter which is located near the tip of the fiber, and an optical system that will locally image the tested area. A long pass filter (e.g., GG475) may be located between the lens and the fibers in order to subtract the Violet/UV light from the image for fluorescence.

The laser ablation system may be located in the area of the imaging sensors 1315 (shown in FIG. 3b).

A pulsed laser beam is passed through a collimating optics, a set of mirrors, a fiber bundle, another mirror, a beam splitter and second focusing optics. There are two optional places to use a motorized adjustable set of mirrors. In the case where a straight solid fiber bundle is used, the laser beam location can be adjusted using the mirrors near the laser, otherwise the adjustable steering mirror may be positioned in front of the beam splitter near the edge of the fiber bundle and its tilted angles controlled remotely. This adjustable set of mirrors receives a set of angles/travels as an output from the image analysis report or a set of points from the physician manually to manipulate the orientation laser beam to selectively impinge on desired locations of malignant tissue to be destroyed.

The image analysis and control unit may use Picture Archiving and Control System (PACS) methods for image archiving and management.

Overcoming deficiencies of prior art colposcope systems, the system according to the present invention provides:

An optical disposable speculum with a working channel for the physician

A small camera with multi spectral internal illumination systems:
  Bright field LEDs (through the lens) illumination
  Dark field LEDs illumination with a specific illumination angle
  An internal UV illumination ("through the lens illumination") for abnormal cell detection by fluorescence or auto fluorescence
  An internal IR illumination ("through the lens illumination")

An opportunity to examine with sufficient resolution fine objects at a short distance with maximum patient protection Optional In-Situ laser ablation of abnormal cells (e.g., cancerous cells)

Figure 2A:
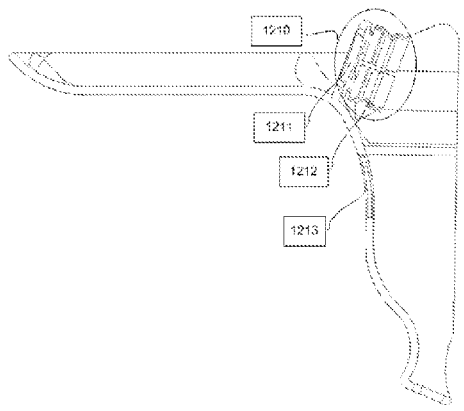
FIG. 2a shows the design of the cover window in the lower part of the optical disposable speculum—cross section view (1210). 1211—Illustrates the front window lens area; 1212—Illustrates the snap area for the image acquisition system; 1213—Illustrates a cut release for the operating buttons of the image acquisition system.
Figure 2B:
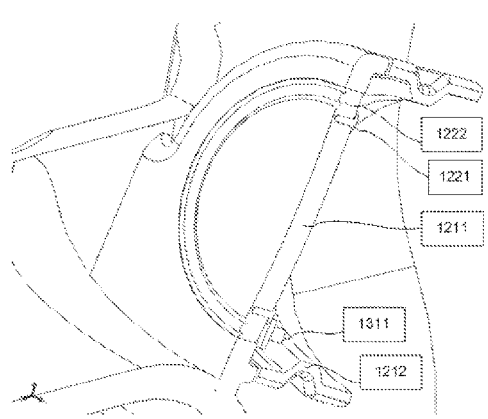
FIG. 2b illustrates the optical disposable front window lens—local view. 1211—Illustrates the optical front window area; 1212—Illustrates the snap area for the image acquisition system; 1222—Illustrates a linear circular collimating lens for a dark field LED ring in the image acquisition system; 1221—Illustrates an elastic layer of material for stray light blocking that may be caused by dark field illumination and bright field illumination; 1311—Illustrates dark field illumination LED ring.

The invention provides an optical disposable speculum that integrates a light collimation element guide for dark field illumination 1222 and an optical window 1211 (shown in FIG. 2b).

The optical disposable speculum may provide a working channel, and an adjustable locking mechanism for lower and upper speculum blades.

The working channel may be used for obtaining a Pap-Smear specimen, and passing working tools (e.g., biopsy tools).

The invention separately provides an optical disposable speculum which is a part of the whole optical design and is assembled on the image acquisition system, thus providing a safe cross contamination protection for the examined patient.

The invention provides a high resolution imaging system which comprises one or more imaging sensors, thus providing high dynamic range image. The importance of such information is that it can be used for computer calculation since such an image with high dynamic range is hard to display or print.

The invention separately may provide a system and methods including a detection algorithm for abnormal cell screening.

The invention may provide a special abnormal cell detection algorithm designed specifically for the uterine cervix.

The objective lens system of the image acquisition system may contain two groups of optical components—group 1320 and group 1340 (shown in FIG. 3b).

Group 1320 may include the aperture stop where the bright field illumination are components located, a group of optical components that is connected to the imaging sensor and a beam splitter and or dichroic mirror. Group 1340 may include a group of optical elements with the disposable optical window 1211 (shown in FIG. 2b).

Between group 1320 and group 1340, in the image acquisition system, a dichroic mirror 1708 (shown in FIG. 3b) may be located to pass the bright field 1313 (e.g., white LED source illumination) (shown in FIG. 3b) with a beam splitter or a UV light source with the dichroic mirror for fluorescence or auto fluorescence (e.g., UV). The location of the multi spectral illumination and or the white/UV illumination source may be on the other side of the dichroic mirror along the objective axis of group 1340.

The optical system may comprise a design of an optical zoom lens system along the optical axis, or a discrete zoom design perpendicular to the optical axis (e.g., slider design).

The image acquisition system is an electro optical element which functions as an integrated system for multi spectral imaging and treatment. The image acquisition system is locked to the optical disposable speculum with a releasable secured mechanical lock.

This invention provides a system and methods for high resolution imaging of the examined area (e.g., uterine cervix). The system provides image analysis for tissue abnormalities.

The invention may be used as an image analysis for tissue abnormalities such as cervical intraepithelial neoplasia (CIN) or invasive cancer.

The system control and analysis unit provides a real time image or live video that is acquired from the examined area. It provides tissue diagnosis and it may provide the ability to ablate, in an accurate manner, the abnormal cancerous cells. Images or live video and analysis results are displayed both to the physician and patient.

The system control and analysis unit may acquire real time images or live video from the uterine cervix. It may ablate, in an accurate manner, the abnormal cancerous cells in the uterine cervix.

The invention provides an assembly verification process (e.g., imaging algorithm) of the assembled optical disposable speculum to the image acquisition system.

The imaging acquisition system acquires color and/or monochrome images. The acquired data of the examined area is analyzed by the image analysis and control unit. The image and analysis control unit outputs a graphical representation of suspicious regions and classification of the detected tissue.

The imaging acquisition system may acquire color and/or monochrome images from the uterine cervix.

Figure 5A:
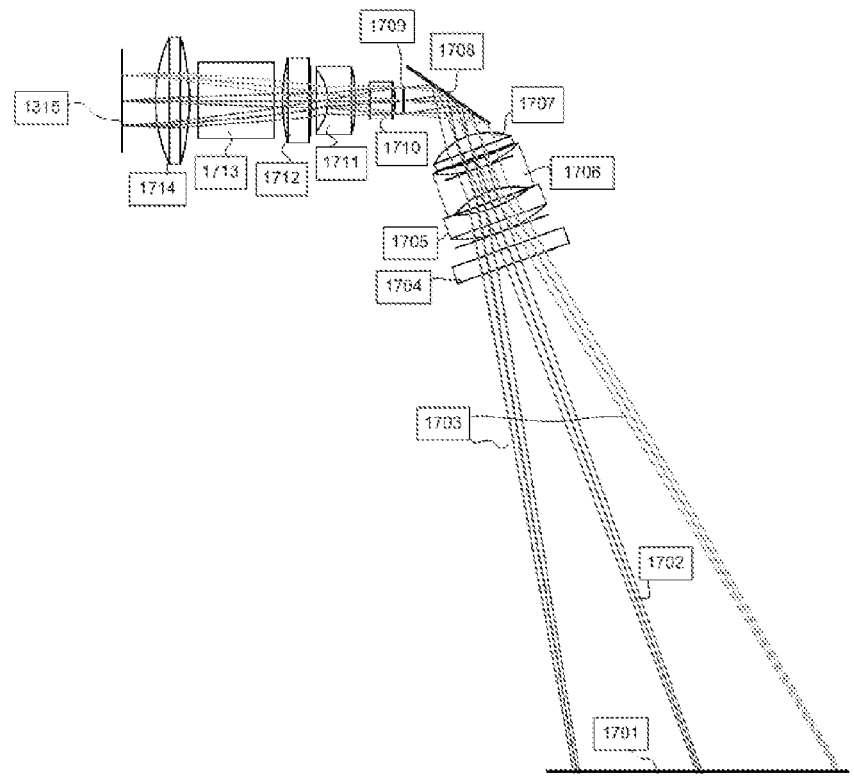
FIG. 5a shows the optical design and chief rays for a one imaging sensor. 1701—Examined area; 1702—Chief return rays; 1703—Marginal return rays; 1704—Window; 1705—Meniscus element; 1706—Bi-concave element; 1707—Bi-convex element; 1708—Dichroic Mirror; 1709—Aperture; 1710—Plano-convex element; 1711—Meniscus element; 1712—Bi-convex element; 1713—Beam Splitter; 1714—Bi-convex element to imaging sensor; 1315—Color imaging sensor.
Figure 5B:
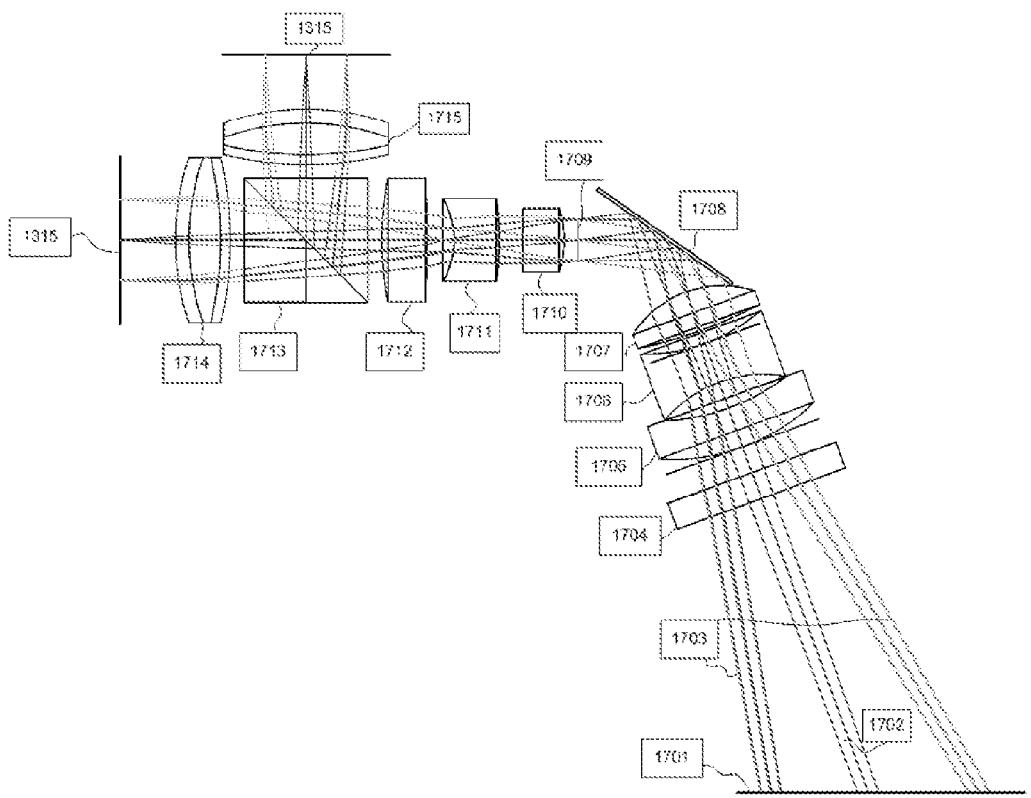
FIG. 5b shows the optical design and chief rays for a two imaging sensor. 1701—Examined area; 1702—Chief return rays; 1703—Marginal return rays; 1704—Window; 1705—Meniscus element; 1706—Bi-concave element; 1707—Bi-convex element; 1708—Dichroic mirror; 1709—Aperture; 1710—Plano-convex element; 1711—Meniscus element; 1712—Bi-convex element; 1713—Beam Splitter; 1714—Bi-convex element to imaging sensor (e.g., color sensor, monochrome sensor); 1715—Bi-convex element to imaging sensor (e.g., color sensor, monochrome sensor); 1315—Imaging sensor (e.g. color sensor, monochrome sensor).

FIGS. 5a and 5b schematically illustrate an optical design for use in an optical head of an image acquisition system for viewing internal cavities (e.g., uterine cervix).

The image acquisition system may be used for video laparoscopy by using a special optical adapter assembled on the image acquisition system.

The image acquisition system and the image analysis control unit may be used for detection of abnormal cells in a laparoscopy procedure.

In FIG. 5a, an optional meniscus lens 1705 comprising a first front optical component of the system may be located in the optical disposable speculum.

In FIG. 5a, a front sub optical system is shown comprising a set of lenses as follows: meniscus 1705, Bi-concave 1706 and Bi-convex 1707.

In FIG. 5a, a rear sub optical system is shown comprising a set of lenses as follows: aperture 1709, plano-convex element 1710, meniscus element 1711, Bi-convex element 1712, beam splitter 1713, Bi-convex element 1714.

In FIG. 5a, at the end of the optical apparatus the imaging sensors 1315 (e.g., CCD or CMOS) are located for image capture.

In FIG. 5b, an optional meniscus lens comprising a first front optical component of the system 1705 is shown.

In FIG. 5b, a front sub optical system is shown comprising a set of lenses as follows: meniscus 1705, Bi-concave 1706 and Bi-convex 1707.

In FIG. 5b, a rear sub optical system is shown comprising a set of lenses as follows: aperture 1709, plano-convex element 1710, meniscus element 1711, Bi-convex element 1712, beam splitter 1713, Bi-convex element 1714 to color or monochrome imaging sensors 1315 (e.g., CCD or CMOS), Bi-convex element 1714 to color or monochrome imaging sensors 1315.

In FIG. 5b, at the end of the optical apparatus, the imaging sensors 1315 are located for image capture.

The optical design may comprise a motor along the optical system axis moving another optical component or components creating optical zoom and focus correction.

The optical design may comprise a motor, perpendicular to the optical system axis moving another optical component or components, with two or more stages. The sliding mechanism replaces an intermediate component or components, thus creating a discrete optical magnification.

On initialization, it is required to go through sensor self-calibration (e.g., white balance). This procedure calibrates the image sensor with internal parameters set for optimal image capture. Image capturing while using these parameters by the sensor avoids unrealistic color or gray level in the final captured image under certain illumination setups (type, mode, etc.) and improves the captured image under a wider range of illumination conditions.

On initialization, the image analysis and control unit initializes the image acquisition system. The image acquisition system starts a self-calibration procedure (e.g., white balance) which avoids acquisition of unrealistic color or gray level. It is the system control and analysis system which responsible for controlling the image acquisition system under certain illumination settings and given tissue conditions (e.g., under use of reflectance reagents).

Figure 6A:
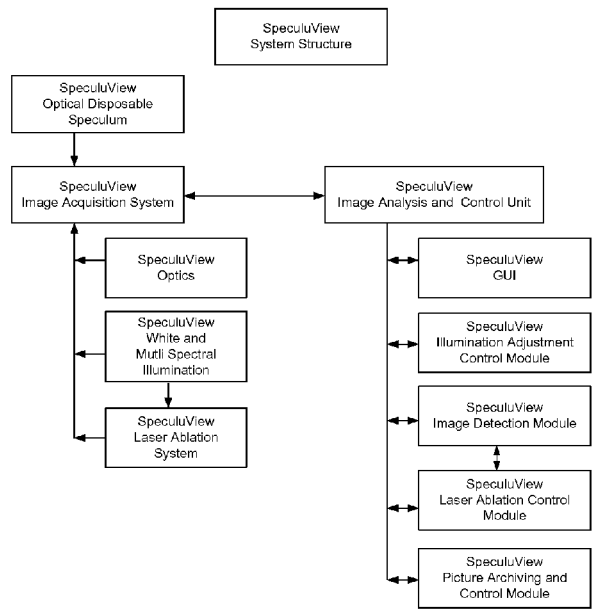
FIG. 6a shows a schematic structure of the SpeculuView system: Optical Disposable Speculum, Image Acquisition System modules, Image Analysis and Control Unit modules.
Figure 6B:
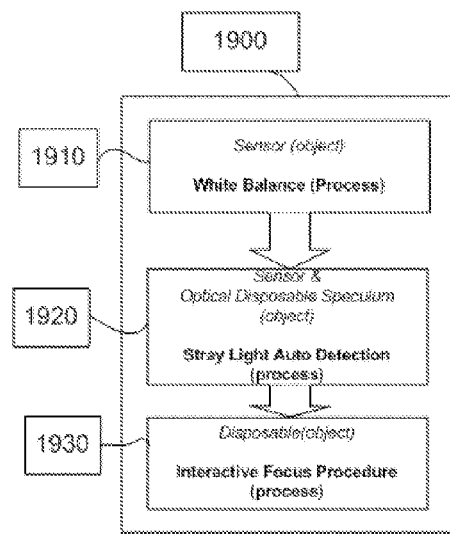
FIG. 6b illustrates the software initialization flow 1900. 1910—Image acquisition system calibration (e.g., white balance) is a process of determining the required amplification degree of the input signal, acquired by the sensor, which yields best image for analysis purposes; 1920—Improper assembly detection, where the image analysis and control unit verifies that the physician assembled and secured the optical disposable speculum in a correct manner; 1930—Interactive focus is a manual procedure which may be needed to be done by the physician for this optical system design.
Figure 6C:
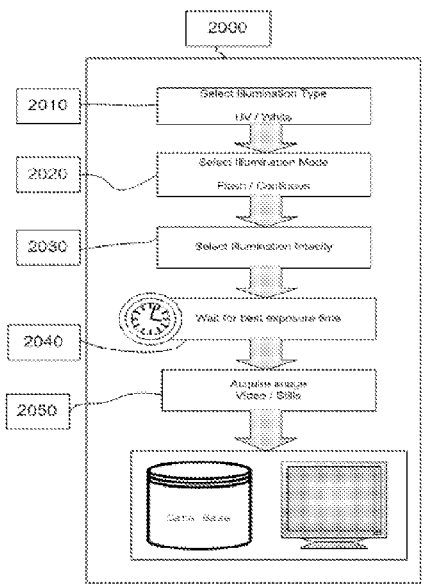
FIG. 6c illustrates image capture algorithm process flow 2000. 2010—Selection light source type for image acquisition, wherein a possible light source may be UV and/or white light; 2020—Selection of light mode: a continuous light or flashed illumination for different illumination effects on the examined tissue for optimal detection; 2030—Selection of illumination amplification for optimal image acquisition; 2040—Determines the time span before the image is considered optimally illuminated for image acquisition; 2050—Acquires the image and analyzes it to verify if there are any changes needed for optimal image acquisition and initiates image re-capture process.
Figure 6D:
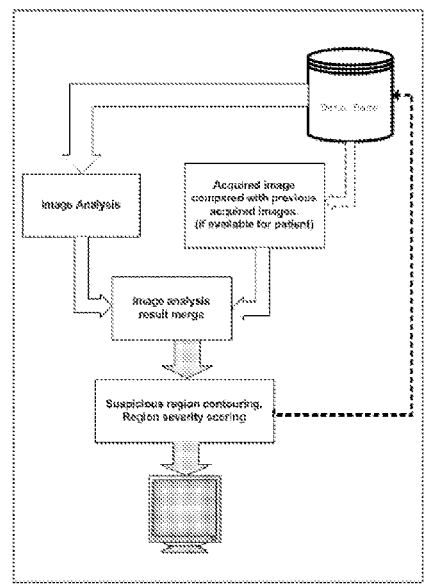
FIG. 6*d* illustrates image analysis, display of suspicious areas by contours and scoring algorithm.

The module involves activation of the illumination source in the working limits within the dynamic range of the system, and recognition of stray light which will indicate that the optical disposable speculum is not properly mounted (FIG. 6b). This module may be identified as: "Stray Light Detection Module" (SLDM).

There are two possible option of focusing:

Option 1: A fixed lens mechanical design that requires an optimal location positioning procedure. It is the physician who guides the optical disposable speculum with the camera head installed in front of the examined area (e.g., uterine cervix) and activates a fine tuning positioning process. In the optimal location positioning procedure, the image analysis and control unit continuously grabs images and produces focus results, which recommend to the physician to make final positioning corrections (FIG. 6b).

Option 2: When using a non-fixed lens mechanical design, an automatic focus mechanism sets an optimal location of the lens. It is the physician who guides the optical disposable speculum with the camera head installed in front of the examined area (e.g., uterine cervix) and activates a fine tuning focus positioning process. In the optimal location positioning procedure, the image analysis and control unit continuously grabs images and produces the best focus results.

There are two main image capture modes. Manual mode requires the physician to control the illumination parameters before the image is acquired and delivered for final analysis. Automatic mode does not require any intervention of the physician with respect to the illumination configuration. An optimal image capture parameters adjustment algorithm continuously grabs images while changing the values of illumination type, mode, intensity and exposure time in order to produce an optimal image for analysis (FIG. 6b).

A numerical analysis for autofluorescence imaging for pathological tissue detects a cancerous area in a given image. The numerical analysis for auto fluorescence imaging includes a pathological tissue algorithm that uses the special characteristics of the reflected ultraviolet light source. The numerical analysis for autofluorescence imaging for pathological tissue detects and renders suspicious regions in a given image, and generates a pathological lesion scoring for the region.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for direct imaging and diagnosing of abnormal cells in a target tissue, comprising:
    a disposable optical speculum;
    an image acquisition system having the speculum assembled on and mechanically secured thereto, the image acquisition system arranged to capture at least one of a single image or multiple images or video of cells within the target tissue using at least one of bright field or dark field ring illumination divided into independently operated segments to obtain a plurality of data sets, wherein the image acquisition system has three separated and independent illuminations: White Bright Field (BF) illumination located near an aperture stop, White Dark Field (DF) illumination for diffusive illumination and divided into segments for independent operation, and Bright Field (BF) multi spectral illumination located behind a dichroic mirror; and
    an image analysis and control unit in communication with the image acquisition system, the image analysis and control unit analyzing the data sets and applying algorithms to the data sets for diagnosing abnormal cells.

2. The system according to claim 1, wherein the disposable optical speculum covers an optical head and yet enables a free working channel for taking a manual biopsy.

3. The system according to claim 1, wherein the image acquisition system includes one or more high resolution imaging sensors which capture different wavelength images of a whole field of the target tissue, wherein the images are injected into separate channels of the image analysis and control unit and presented separately on a screen.

4. The system according to claim 1, wherein the optical disposable speculum is designed for single use to protect from cross-contamination and the image acquisition system is designed for multiple uses.

5. The system according to claim 1, wherein the image acquisition system further comprises a laser ablation module with a 2-D tilted mirror system to enable accurate ablation of abnormal cells, wherein the laser ablation module uses the data sets to eliminate the diagnosed abnormal cells, and the image acquisition system is designed to stop ablation when it is detected that abnormal cells no longer exist in the image.

6. The system according to claim 5, wherein the laser ablation module comprises an Infra Red/Green/Ultra Violet short pulse laser beam guided via a high power fiber to the target tissue using an imaging lens for focusing the pulse beam with enough pulse energy and pulse peak power to remove the abnormal cells.

7. The system according to claim 1, wherein the optical disposable speculum includes an optical window provided with a layer of elastic material which creates a coupling between the optical disposable speculum and the image acquisition system to prevent stray light.

8. The system according to claim 1, further comprising a locking mechanism between the optical disposable speculum and the image acquisition system to assure image acquisition without distortions.

9. The system according to claim 1, wherein the image acquisition system further comprises a zooming lens that can be implemented by using a miniature piezo or electric motor.

10. The system according to claim 1, wherein the image acquisition system further comprises at least one of automatic, semi-automatic and manual illumination LEDs and a laser diode (LD) adjustment.

11. The system according to claim 1, wherein the image acquisition system comprises one of a single or dual sensor imaging system with color and monochrome CMOS or CCD, and an illumination system based on one of LEDs or laser diode (LD).

12. The system according to claim 11, wherein the illumination system comprises bright field illumination, dark field external ring illumination, and one of a UV LED source for fluorescence or autofluorescence or a multi-spectral source.

13. The system according to claim 11, wherein the illumination system includes a ring of white/monochromatic LEDs positioned near a lens aperture in order to optimize the delivery of light into the target tissue with minimum angle of incidence to optimize the reflection from the tissue using a second part of an objective lens.

14. The system according to claim 1, wherein the image acquisition system achieves depth perception in an acquired image by using at least one of a large depth of field, a contiguous zoom feature to receive a sequence of different images of the same X,Y position at different focal planes, and dark field illumination applied at different illumination angles using a ring external illumination system.

15. The system according to claim 1, wherein the optical disposable speculum integrates a light collimation element guide for dark field illumination with an optical window.

16. The system according to claim 1, wherein the image acquisition system includes a camera apparatus comprising a camera, a lens attached to the camera, and a long pass filter which will subtract the UV/near UV light in order to obtain a fluorescence image.

17. The system according to claim 10, wherein the illumination system includes a light source having one of an external strobe or camera electronic shutter to control the camera exposure time and prevent any saturation in the imaging system.

18. The system according to claim 1, further comprising a detector for warning of undesired stray light generated by improper assembly of the optical disposable speculum to the image acquisition system.

19. The system according to claim 1, wherein each optical disposable speculum includes an RFID tag to provide a unique identification for each optical disposable speculum and ensure use of a new optical disposable speculum when desired.

* * * * *